(12) United States Patent
Blochet et al.

(10) Patent No.: US 10,013,534 B2
(45) Date of Patent: Jul. 3, 2018

(54) PILL DISPENSING SYSTEM FOR MONITORING COMPLIANT RECEIPT OF PILLS BY A PATIENT

(71) Applicants: Martial Blochet, Saint Germain en Laye (FR); Olivier Triqueneaux, Paris (FR)

(72) Inventors: Caroline Blochet, Saint Germain en Laye (FR); Martial Blochet, Saint Germain en Laye (FR); Olivier Triqueneaux, Paris (FR)

( * ) Notice: Subject to any disclaimer, the term of this patent is extended or adjusted under 35 U.S.C. 154(b) by 463 days.

(21) Appl. No.: 14/127,660

(22) PCT Filed: Dec. 19, 2012

(86) PCT No.: PCT/IB2012/002753
§ 371 (c)(1),
(2) Date: Dec. 19, 2013

(87) PCT Pub. No.: WO2014/096879
PCT Pub. Date: Jun. 26, 2014

(65) Prior Publication Data
US 2014/0288942 A1 Sep. 25, 2014

(51) Int. Cl.
*G06F 19/00* (2018.01)
*A61J 7/04* (2006.01)

(52) U.S. Cl.
CPC .......... *G06F 19/3456* (2013.01); *A61J 7/04* (2013.01); *A61J 7/0481* (2013.01); *G06F 19/3462* (2013.01); *A61J 2200/30* (2013.01)

(58) Field of Classification Search
CPC combination set(s) only.
See application file for complete search history.

(56) References Cited

U.S. PATENT DOCUMENTS 5,412,372 A * 5/1995 Parkhurst .............. A61J 7/0481
221/15
5,805,051 A * 9/1998 Herrmann .............. A61J 7/0481
221/2

(Continued)

FOREIGN PATENT DOCUMENTS

GB 2344194 A * 5/2000 ............ A61J 7/0069
GB 2344194 A * 5/2000 ............ A61J 7/0069

(Continued)

*Primary Examiner* — Gene O Crawford
*Assistant Examiner* — Stephen L Akridge
(74) *Attorney, Agent, or Firm* — Bachman & LaPointe, P.C.

(57) ABSTRACT

A pill dispensing system for monitoring compliant receipt of pills by a patient, comprising a base unit having an area adapted to receive a pill container, the base unit comprising a microprocessor and a power supply, the pill container comprising a plurality of breakable closures each sealing a respective one of the pill compartments, each breakable closure comprising a breakable conductor being adapted to break upon breaking of the breakable closure of a respective one of the pill compartments and to generate a first pill compartment opening signal on the microprocessor, said base unit further comprising a plurality of optical detectors, each optical detector being associated with a respective one of the pill compartments of the pill container and being adapted to generate a second pill compartment opening signal on the microprocessor upon the breaking of the breakable closure of a respective one of the pill compartments.

16 Claims, 6 Drawing Sheets

(56) References Cited

U.S. PATENT DOCUMENTS

| | | | | |
|---|---|---|---|---|
| 6,574,166 B2* | 6/2003 | Niemiec | ............... | A61J 7/0481 206/531 |
| 2007/0296598 A1* | 12/2007 | Kim | ................... | G06F 19/3462 340/572.8 |
| 2008/0105588 A1* | 5/2008 | Tran | ................... | G06F 19/3462 206/534 |
| 2008/0109510 A1* | 5/2008 | Gerlt | ........................ | A61J 7/04 709/201 |
| 2009/0065522 A1* | 3/2009 | Benouali | ................. | A61J 1/035 221/7 |
| 2009/0194452 A1* | 8/2009 | Hession | .................. | A61J 1/035 206/531 |
| 2010/0049361 A1* | 2/2010 | Bertrand | ............... | A61J 7/0481 700/232 |
| 2011/0155602 A1* | 6/2011 | Sterry | ................... | A61J 7/0436 206/459.1 |

FOREIGN PATENT DOCUMENTS

| | | | | |
|---|---|---|---|---|
| GB | 2463054 A | * | 3/2010 | ............... A61J 7/04 |
| GB | 2463054 A | | 3/2010 | |
| WO | 2008086628 A1 | | 7/2008 | |
| WO | 2012111034 A1 | | 8/2012 | |
| WO | WO-2012111034 A1 | * | 8/2012 | .............. A61J 1/035 |

* cited by examiner

PILL DISPENSING SYSTEM FOR MONITORING COMPLIANT RECEIPT OF PILLS BY A PATIENT

BACKGROUND

The present invention relates to the field of pill dispensing systems and more particularly to a pill dispensing system for monitoring compliant receipt of pills by a patient.

Nowadays, it is more and more common that a patient needs to take a significant amount of medication during a certain period of time and sometimes at certain periods during a day.

In order to comply with the increased medication needs and appropriately organize the prescribed medication especially in the case that the medication is issued in the form of pills, a patient uses pill containers having various configurations of pill compartments. The quantity of pills being contained in each one of the pill compartments depends on the prescribed medication corresponding to each patient.

In an example, the pill containers are organized in an array of pill compartments having four columns and seven rows. Particularly, a pill compartment corresponds to each column and row intersection point. Each column is labelled such that it indicates a certain period during the day (morning, midday, afternoon, evening) while each row is labelled such that it indicates a certain day of a week. Also, the pill compartments are sealed by closures such that the pills being contained into each one of the pill compartments are secured.

However, the patients often neglect to take their pills at the prescribed date and time. This fact has a negative effect on the health of the patients, especially when their life depends on a strict compliant receipt of the prescribed pills.

In order to reduce the above mentioned negative health effects, the monitoring of the compliant receipt of the pills by a patient is necessary. For that purpose, pill dispensing systems for monitoring the compliant receipt of the pills by a patient are used. Particularly, the above mentioned pill dispensing systems are adapted to detect that a patient has received his pills at the prescribed date and time.

U.S. Pat. No. 6,574,166 discloses an example of such pill dispensing systems. Particularly, the dispensing system of the above mentioned patent comprises a base unit having an area adapted to receive a pill container. The pill container comprises an array of pill compartments and a plurality of breakable closures, each sealing a respective one of the pill compartments. Furthermore, each breakable closure comprises a breakable conductor being adapted to break upon breaking of the breakable closure. The above mentioned pill dispensing system also comprises a microprocessor being connected to each one of the breakable conductors such that it can sense the accessing of each one of the pill compartments by a patient. The microprocessor actually senses a change of electrical signal resulting from the cutting of the electric current being transferred through each one of the breakable conductors to the microprocessor. The above mentioned cutting of the electric current takes place after the breaking of a respective one of the breakable conductors after the accessing by a patient of the pill compartment along which it passes the respective one of the breakable conductors.

However, the above mentioned sensing does not occur for a respective one of the pill compartments when the respective one of the breakable conductors that passes along the latter pill compartment presents defects. For example, if a respective one of the breakable conductors is broken during manufacturing, it is implicit that after the accessing of the corresponding pill compartment there will be no change in the electrical signal being received by the microprocessor. Particularly, in the case that the breakable conductor is broken during manufacturing, no electric current is transmitted by the above mentioned broken breakable conductor to the microprocessor neither before nor after the accessing of the corresponding pill compartment by a patient.

Thus, it goes without saying that a possible defect in one or more breakable conductors passing along one or more breakable closures of one ore more of the corresponding pill compartments of a pill container will significantly influence the monitoring of the compliant receipt of the pills by a patient and may end up being very dangerous for the health of the latter.

Accordingly, there is a need for more reliable pill dispensing systems for monitoring the compliant receipt of pills by a patient.

SUMMARY

It is an object of the present invention to provide a more reliable pill dispensing system for monitoring the compliant receipt of pills by a patient.

This and other objects of the invention are achieved by means of a pill dispensing system for monitoring compliant receipt of pills by a patient comprising a base unit having an area adapted to receive a pill container, a pill container comprising an array of a plurality of pill compartments. At least one pill compartment of the pill container contains at least one pill, said area comprises an array of a plurality of compartments adapted to receive at least one of said pill compartments, and the base unit of the pill dispensing system comprises a microprocessor and a power supply. The pill dispensing system further comprises at least one breakable closure, sealing at least one of said pill compartments. The pill dispensing system further comprises some means for detecting the breaking of the breakable closure of a respective one of the pill compartments and for generating a first pill compartment opening signal on the microprocessor upon breaking of the breakable closure of a respective one of the pill compartments. The pill dispensing system further comprises some means for detecting the removal of the at least one pill from one of the pill compartment upon the breaking of the breakable closure of the respective one of the pill compartments and for generating a second pill compartment opening signal on the microprocessor upon the removal of the at least one pill from one of the pill compartments.

The fact that both a first pill compartment opening signal and a second pill compartment opening signal are generated on the microprocessor upon the breaking of the breakable closure of a respective one of the pill compartments increases the reliability of the pill dispensing system with regard to the prior art pill dispensing systems. Particularly, in the prior art systems only one pill compartment opening signal is generated on the microprocessor by the breaking of the breakable conductors as explained in the background art.

The term "compartment" refers to all type of area able to accommodate one or several pill(s) such as, but not exclusively, cells, recess, receiving track.

Advantageously, the pill dispensing system according to claim 1, wherein said means for detecting the removal of the at least one pill from one of the pill compartment upon the breaking of the breakable closure of the respective one of the pill compartments and for generating a second pill compartment opening signal on the microprocessor comprise a plurality of optical detectors, each optical detector being associated with a respective one of the pill compartments of the pill container when the pill container is received by said base unit.

In an embodiment, each one of the optical detectors of the pill dispensing system comprises an emitter and a corresponding receiver being proximately disposed on a lateral side of a respective one of the recesses so that to correspond to a respective one of the pill compartments When pill container is fixed to the base unit. The emitter emits a light beam which is reflected at a surface of the at least one pill when the associated pill compartment comprises at least one pill and being received by the receiver. The optical detector is adapted to generate the second pill compartment opening signal in response to the detection of a variation of the reflected light beam occurring after the removal of the at least one pill from the respective one of the pill compartments upon the breaking of the breakable closure of the respective one of the pill compartments.

Advantageously, said means for detecting the removal of the at least one pill from one of the pill compartment upon the breaking of the breakable closure of the respective one of the pill compartments and for generating a second pill compartment opening signal on the microprocessor comprise some vibrators, each vibrators being arranged to be associated with a respective one of the pill compartments of the pill container when the pill container is received by said base unit.

Advantageously, said means for detecting the breaking of the breakable closure of a respective one of the pill compartments and to generating a first pill compartment opening signal on the microprocessor comprise some breakable conductor, each breakable conductor being provided with the at least one breakable closure sealing at least one of said pill compartments and arranged to be associated with a respective one of the pill compartments of the pill container.

Advantageously, said means for detecting the breaking of the breakable closure of a respective one of the pill compartments and to generating a first pill compartment opening signal on the microprocessor comprise an accelerometer.

Advantageously, the compartments of said area are arranged to form an array of a plurality of recesses equivalent to the array of the plurality of pill compartments of the pill container.

In another embodiment, the base unit of the pill dispensing system comprises a RF transceiver being adapted to communicate at least one of the first pill compartment opening signal and the second pill compartment opening signal to an outside server. The RF transceiver operates for example in Bluetooth/Wi-Fi/GPRS/Sigfox mode. The expression "outside server" comprises an external device, a remote database or an external system such as a remote information platform.

In another embodiment, the base unit comprises a memory and a clock, wherein the memory is adapted to store information relating to the time of breaking of the breakable closure of a respective one of the pill compartments.

Furthermore, in an embodiment, the base unit of the pill dispensing system comprises a wireless communication module arranged to allow wireless communication with an outside server.

In another embodiment, an RFID tag is affixed to the pill container of the pill dispensing system and an RFID tag reader is affixed to the base unit of the pill dispensing system for the purpose of identification of the pill container by the base unit.

In another embodiment, a RFID tag is affixed to the base unit for the purpose of identification of the base unit by a RFID tag reader. Advantageously, the RFID tag reader is affixed to the base unit.

In another embodiment, the pill dispensing system comprises a plurality of light emitting diodes, each light emitting diode being disposed proximate to a respective one of the pill compartments for illuminating the respective one of the pill compartments at a predetermined time of scheduled receipt of the pills contained in the respective one of the pill compartments.

Advantageously, the pill container is a single-use container.

According to a particular embodiment, the pill dispensing system comprises a pill container comprising an array of a plurality of pill compartments, and a base unit having an area adapted to receive the pill container, said area comprising an array of an equivalent plurality of recesses. At least one pill compartment of the pill container contains at least one pill and the base unit of the pill dispensing system comprises a microprocessor and a power supply. The pill container further comprises a plurality of breakable closures, each one of them sealing a respective one of the pill compartments. Each breakable closure comprises a breakable conductor which is adapted to break upon breaking of the breakable closure of a respective one of the pill compartments and to generate a first pill compartment opening signal on the microprocessor. The pill dispensing system is characterized in that the base unit further comprises a plurality of optical detectors, each optical detector being associated with a respective one of the pill compartments of the pill container and being adapted to generate a second pill compartment opening signal on the microprocessor upon the breaking of the breakable closure of a respective one of the pill compartments.

According to another aspect, the invention relates to a method of management of taking pills by a patient in accordance with a prescription with a pill dispensing system according to anyone of the preceding claims, the pill container and the base unit being respectively provided with a RFID tag for the purpose of identification of the pill container by the base unit and the identification of the base unit, said method comprising the following steps:
  recording of the identifier of the pill container recorded in the RFID tag and a plan of taking of pills established in accordance with the identity of patient and with data of prescription in a remote server,
  authentification of the pill container by the base unit when the pill container is paired to the base unit by means of the RFID tags of the pill container and the base unit,
  transmission of the plan of taking from the remote server to the unit base in response to a signal from base unit.

Advantageously, the method further comprises a step of transmitting information about taking or not of pills from the base unit to the remote server.

BRIEF DESCRIPTION OF THE DRAWINGS

The above objects and characteristics of the present invention will be more apparent by describing an/several embodiments of the present invention in detail with reference to the accompanying drawings, in which.

DETAILED DESCRIPTION

Figure 1:
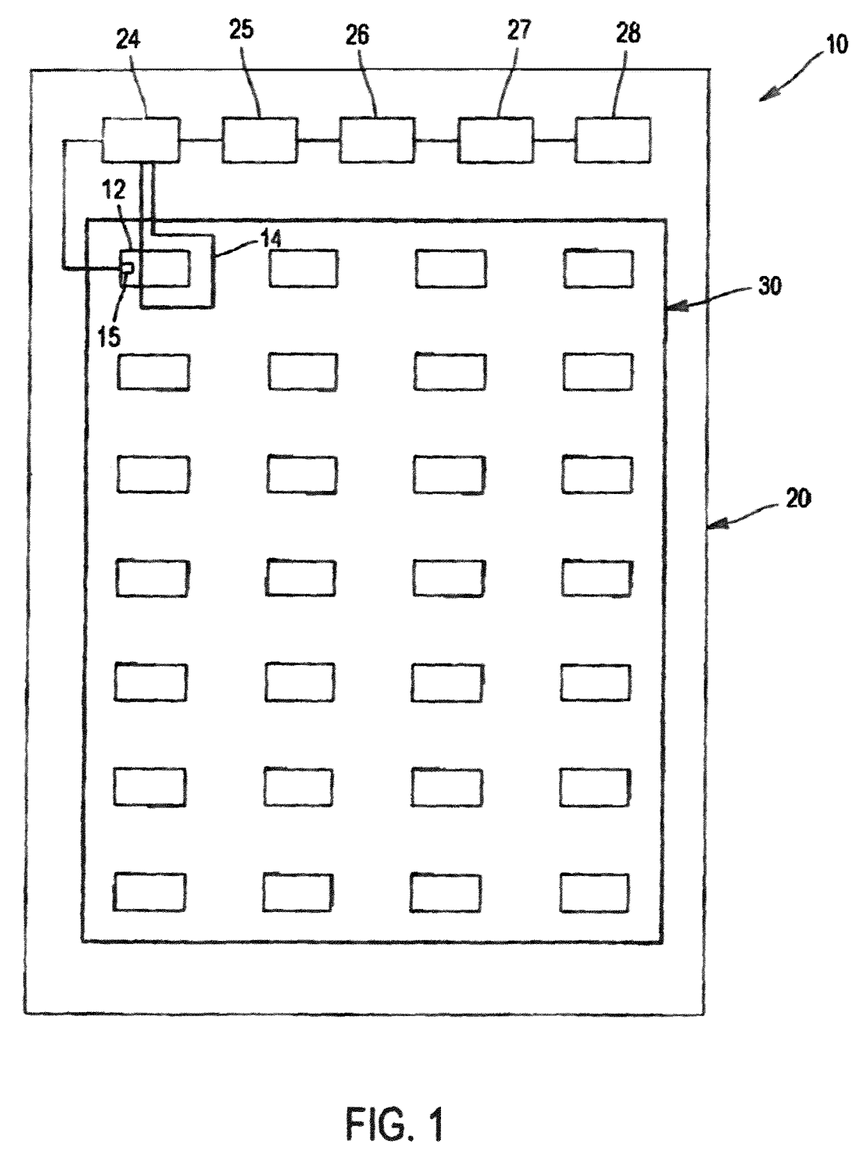
FIG. 1 illustrates a diagram of the pill dispensing system according to an embodiment of the invention.

FIG. 1 illustrates an embodiment of a pill dispensing system 10 for monitoring compliant receipt of pills by a patient. The pill dispensing system 10 includes a base unit 20 and a pill container 30. The base unit 20 has an area 11 (see FIG. 2 which illustrates an exploded view of the pill dispensing system of the embodiment of FIG. 1) adapted to receive the pill container 30. Particularly, the pill container 30 comprises an array of pill compartments 12 whilst the area 11 comprises a plurality of recesses 18 (see FIG. 2). Each recess 18 is shaped and sized such that it receives a respective one of the pill compartments 12. In an example, the pill container 30 comprises an array of twenty eight pill compartments having four columns and seven rows. In that example each column may be labelled for a certain time period during the day (morning, midday, evening, bedtime) while each row may be labelled for a certain day of the week such that each pill compartment 12 corresponds to a certain day of the week and to a certain time period during the day. Each one of the pill compartments 12 may contain at least one pill being prescribed to the patient.

Figure 3:
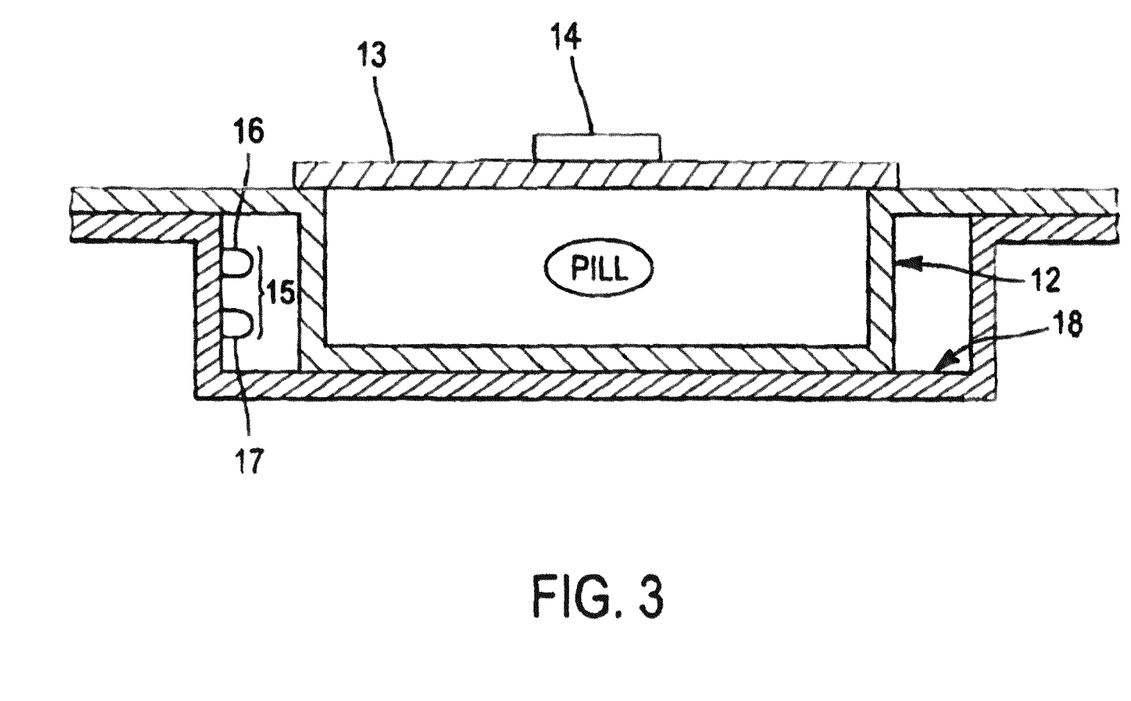
FIG. 3 illustrates a partial cross-section of a pill compartment according to the embodiment of FIG. 1.

Furthermore, each one of the pill compartments 12 of the embodiment of FIG. 1 is sealed by a breakable closure 13 (see FIG. 3) in order to secure the at least one pill being contained therein. Particularly, FIG. 3 shows a partial cross-section of a respective one of the pill compartments 12 according to the embodiment of FIG. 1 wherein a breakable closure 13 seals a respective one of the pill compartments 12. As shown in FIG. 3, the breakable closure 13 comprises a breakable conductor 14. The breakable conductor 14 is adapted to break upon breaking of the breakable closure 13. Particularly, the breakable conductor 14 passes along the breakable closure 13 of a respective one of the pill compartments 12 and breaks when the breakable closure 13 breaks as a patient accesses to the respective one of the pill compartments 12. The breakable closure 13 may be made by a conductive material (e.g. aluminium foil) or by a nonconductive material (e.g. paper).

In the embodiment of FIG. 1, the breakable conductor 14 is connected to a microprocessor 24 such that the breaking of the breakable conductor 14 after the accessing of a respective one of the pill compartments 12 generates a first pill compartment opening signal on the microprocessor 24. Particularly, the accessing of the respective one of the pill compartments 12 is performed by the breaking of the breakable closure 13 of the respective one of the pill compartments 12, which breakable closure 13 comprises the breakable conductor 14. FIG. 1 illustrates only one of the breakable conductors 14 passing along a respective one of the breakable closures 13 of a respective one of the pill compartments 12 (top left pill compartment shown in FIG. 1). However, it is important to clarify that a breakable conductor 14 passes along the breakable closures 13 of each one of the pill compartments 12 of the pill container 30. In an example, after the accessing of twenty eight pill compartments by a patient, twenty eight different first pill compartment opening signals will be generated on the microprocessor 24. Thus, a first pill compartment opening signal is generated on the microprocessor 24 after the breaking of each one of the breakable conductors 14 upon the accessing of each one of the corresponding pill compartments 12. Particularly, each one of the first pill compartment opening signals indicates that the respective one of the pill compartments 12 is accessed by a patient. A first pill compartment opening signal is generated as a result of the change of the electric current being transmitted by the breakable conductors 14 to the microprocessor 24 after the breaking of the breakable conductors 14. Particularly, before the breaking of a respective one of the breakable conductors 14, electric current is transmitted to the microprocessor 24 through the respective one of the breakable conductors 14 while after the breaking of the respective one of the breakable conductors 14, the electric current is cut and thus the microprocessor 24 does not receive electric current.

In an example, the breakable conductors 14 covering the breakable closures 13 of each one of the pill compartments 12 are formed by thin wires being adhered to an adhesive layer. The adhesive layer further adheres on the breakable closures 13 corresponding to each one of the pill compartments 12 such that the thin wires pass along each one of the breakable closures 13. The thin wires have terminals that are connected to the microprocessor 24 when the pill container 30 is mounted on the base 20. Alternatively, the breakable conductors 14 are formed by printing a printed circuit onto a non-conductive substrate which is applied on the breakable closures 13. The conductive pathways of the printed circuit form the breakable conductors 14 such that each one of the breakable conductors 14 passes along each one of the breakable closures 13 sealing a respective one of the pill compartments 12. The conductive pathways have terminals that are connected to the microprocessor 24 when the pill container 30 is mounted on the base 20.

Advantageously, in the embodiment of FIG. 1, the base unit 20 further comprises a plurality of optical detectors 15. Each optical detector 15 is associated with a respective one of the pill compartments 12 of the pill container 30 and is adapted to generate a second pill compartment opening signal on the microprocessor 24 after the accessing of the respective one of the pill compartments by the patient. The accessing of the respective one of the pill compartments 12 by the patient is performed by the breaking of the breakable closure 13 of the respective one of the pill compartments 12. FIG. 1 illustrates only one optical detector 15 associated with a respective one of the pill compartments 12 (top left pill compartment shown in FIG. 1). However, it is important to clarify that an optical detector 15 corresponds to each one of the pill compartments 12 (see FIG. 2). Thus, a second pill compartment opening signals is generated on the microprocessor 24 after the accessing of each one of the pill compartments 12. In an example, after the accessing of twenty eight pill compartments by a patient, twenty eight different second pill compartment opening signals will be generated on the microprocessor 24. Particularly, each one of the second pill compartment opening signals indicates that the respective one of the pill compartments 12 is accessed by a patient.

The advantage of the generation of the above mentioned second pill compartment opening signal is that even if the breakable conductors 14 covering the breakable closures 13 present defects, and thus the generation of a first pill compartment opening signal on the microprocessor 24 is not achieved, the detection of the opening of a respective one of the pill compartments by the microprocessor 24 will be still possible by the second pill compartment opening signal being generated on the microprocessor 24. Thus, the reliability of the pill dispensing systems for monitoring compliant receipt of pills by a patient by detecting the accessing of each one of the pill compartments of a pill container is improved when two different pill compartment opening signals are generated, instead of only one as is the case in the prior art systems, after the accessing of each one of the pill compartments.

In an embodiment, each optical detector 15 which is associated with a respective one of the pill compartments 12 of the pill container 30 comprises an emitter 16 and a receiver 17. The emitter 16 and the receiver 17 are disposed on a lateral side of a respective one of the recesses 18 corresponding to a respective one of the pill compartments 12 of the base unit 20 (see FIG. 3), which pill compartments 12 may contain at least one pill. The emitter 16 is disposed such that when the pill container 30 is mounted on the base unit 20 it emits a light beam (not shown in FIG. 3) which is reflected at a surface of the at least one pill being contained in the respective one of the pill compartments 12. It is important to note that each one of the pill compartments 12 is made of a material transparent to light such that the light beam being emitted by the emitter 16 passes through the pill compartments 12 without being reflected at the surface of the pill compartments 12. In an example, the pill compartments are made by a transparent plastic material. After the reflection at the surface of the at least one pill, the light beam is received by the receiver 17. The optical detector 15 is adapted to generate a second pill compartment opening signal in response to the detection of the variation of the reflected light beam occurring after the removal of the at least one pill from the respective one of the pill compartments 12. In an embodiment, the emitter 16 is an infrared Light Emitting Diode (LED) while the receiver 17 is an infrared photodiode being connected to the microprocessor 24. Particularly, before the removal of the at least one pill from the respective one of the pill compartments 12, the infrared photodiode receives the light beam being reflected on the surface of the at least one pill and further converts the received light beam into electric current being transferred to the microprocessor 24. However, when the at least one pill is removed from the respective one of the pill compartments 12 after the accessing of the latter by a patient, the amount of the reflected light being received by the infrared photodiode is modified and so does the electric current which is transferred to the microprocessor 24. Thus, a second pill compartment opening signal is generated on the microprocessor 24 as a result of the variation of the electric current being sensed by the microprocessor 24 after the removal of the at least one pill which takes place after the accessing of the respective one of the pill compartments 12 by the patient. The above mentioned accessing occurs by the breaking of the breakable closure 13 of the respective one of the pill compartments 12.

In another embodiment, the emitter 16 and the receiver 17 of the optical detector 15 are disposed on two opposite lateral sides of a respective one of the recesses 18. The emitter 16 transmits a light beam to the receiver 17 such that when the pill container 30 is mounted on the base unit 20, the light beam is transversely transmitted from one of the lateral sides to the opposing lateral side of a respective one of the pill compartments 12 corresponding to the respective one of the recesses 18. It is important to note that each one of the pill compartments 12 is made of a material transparent to light such that the light beam being transmitted by the emitter 16 to the oppositely disposed receiver 17 passes through the pill compartments 12 without being reflected at the lateral sides. In an example, the pill compartments are made by a transparent plastic material. Also, it is important to note that in this embodiment, the transversely transmitted light beam is not reflected on the surface of the at least one pill contained in a respective one of the pill compartments 12 but it passes above the surface of this at least one pill. The second pill compartment opening signal is generated on the microprocessor 24 as a result of the interruption of the transmission of the light beam to the receiver 17 being caused by the insertion of a finger of a user into the respective one of the pill compartments 12 upon the breaking of the corresponding breakable closure 13. In an embodiment, the emitter 16 is an infrared Light Emitting Diode (LED) while the receiver 17 is an infrared photodiode being connected to the microprocessor 24. Before the insertion of a finger of a user into the respective one of the pill compartments 12, the infrared photodiode receives the light beam being transversely transmitted by the LED and further converts the received light into electric current being transferred to the microprocessor 24. However, after the insertion of the finger of a user into the respective one of the pill compartments 12, the light beam being transversely transmitted to the photodiode is interrupted and thus no electric current is transferred to the microprocessor 24 until the finger is removed from the pill compartment 12. Thus, the second pill compartment opening signal is generated on the microprocessor 24 as a result of a short interruption of the electric current being sensed by the microprocessor 24 when a respective one of the pill compartments 12 is accessed by a patient.

It is important to note that the base unit 20 in the embodiment of FIG. 1 also comprises a power supply 28 for providing power to each one of the electrical components of the base unit 20. In an embodiment, the power supply 28 is a battery. In an example, the base unit 20 comprises a LED being connected to the battery and being adapted to emit a continuous optical signal when the level of the battery is low.

In an embodiment, the microprocessor 24 is adapted to generate an alarm signal towards the patient in the case that only a first pill compartment opening signal or only a second pill compartment opening signal is generated in the microprocessor 24 when a respective one of the pill compartments 12 of a pill container 30 is accessed by a patient. Particularly, if there are defects in the optical detector 15 corresponding to the respective one of the pill compartments 12, only a first pill compartment opening signal will be generated on the microprocessor 24 after the accessing of the respective one of the pill compartments 12. In contrast, if there are defects in the breakable conductor 14 corresponding to the respective one of the pill compartments 12, only a second pill compartment opening signal will be generated on the microprocessor 24 after the accessing of the respective one of the pill compartments 12. The microprocessor 24 is connected to a signalling device such that an acoustic signal or an optical signal is generated towards the patient when only a first pill compartment opening signal or only a second pill compartment opening signal is generated on the microprocessor 24 after the accessing of a respective one of the pill compartments 12. The signalling device may comprise an acoustical source (e.g. a buzzer) or a light source (e.g. a LED). In that way, the patient is informed that either the breakable conductor 14 or the optical detector 15 of the respective one of the pill compartments 12 present defects. In an embodiment, the acoustic or optical signal in the case that only a first pill compartment opening signal is generated on the microprocessor 24 after the accessing of a respective one of the pill compartments 12, is different from the acoustical or optical signal in the case that only a second pill compartment opening signal is generated on the microprocessor 24 after the accessing of the respective one of the pill compartments 12. In that way, the patient can distinguish if the defects are presented in the breakable conductor 14 or in the optical detector 15 corresponding to the respective one of the pill compartments 12.

It is important to note that the pill dispensing system 10 can monitor the compliant receipt of pills by a patient even if only a first pill compartment opening signal or only a second pill compartment opening signal is generated on the microprocessor 24 when a respective one of the pill compartments 12 is accessed by a patient. In an example, the base unit 20 does not comprise optical detectors 15 and thus the above mentioned monitoring is performed only by the generation of a first pill compartment opening signal on the microprocessor 24 after the breaking of each one of the breakable conductors 14 passing along each one of the respective breakable closures 13 of the pill compartments 12. In another example, the base unit 20 comprises optical detectors 15 while the breakable closures 13 of the pill compartments 12 do not comprise breakable conductors 14. Thus, the above mentioned monitoring is performed only by the generation of a second pill compartment opening signal being generated on the microprocessor 24 by each one of the optical detectors 15 when a respective one of the pill compartments 12 is accessed by a patient.

In an embodiment, the base unit 20 comprises a RF transceiver 25 which is adapted to communicate at least one of the first pill compartment opening signal and the second pill compartment opening signal to an outside server. It is important to note that each of these two signals provide information about the fact that a respective one of the pill compartments 12 of the pill container 30 has been accessed by a patient and thus the respective one of the pill compartments 12 has been opened. Particularly, the RF transceiver 25 is connected to the microprocessor 24 and receives at least one of the first pill compartment opening signal and the second pill compartment opening signal in order to transmit it to the outside server. In case of defects presented in at least one of the breakable conductors 14 corresponding to at least one of the pill compartments 12, the RF transceiver 25 will receive at least one second pill compartment opening signal indicating the accessing of the at least one of the pill compartments 12. In contrast, if there are defects in at least one of the optical detectors 15 corresponding to at least one of the pill compartments 12, the RF transceiver 25 will receive at least one first pill compartment opening signal indicating the accessing of the at least one of the pill compartments 12. The outside server may be located on a pharmacy or on a hospital or more generally on a web server and provide information regarding the accessing of each one of the pill compartments 12 to a pharmacist or a physician or to a third party concerned about the compliant receipt of pills by the patient. The RF transceiver 25 may operate for example in Bluethooth/Wi-Fi/GPRS/Sigfox mode.

In an embodiment, the base unit 20 comprises a memory 26 and a clock 27. The memory 26 is connected to the microprocessor 24 and to the clock 27 such that it stores information regarding the time and the date of accessing of each one of the pill compartments 12 of the pill container 13 by the user. The information regarding the time and date of accessing of each one of the pill compartments 12 of a pill container 30 is determined by the time and date of generation of the first pill compartment opening signal and the second pill compartment opening signal in the microprocessor 24 for each one of the pill compartments 12.

In another embodiment, a RFID tag is affixed to the pill container 30 and an RFID tag reader is affixed to the base unit 20 for the purpose of identification of the pill container 30 by the base unit 20. Also, in an embodiment, a RFID tag is affixed to the base unit 20 for the purpose of identification of the base unit 20 by the RFID tag reader affixed to the base unit 20. Data regarding the identity of the pharmacist who has delivered the pill dispensing system 10 to the patient and also regarding the identity of the patient who has received the pill dispensing system is encoded into the RFID tag being affixed to the base unit 20. The RFID tag affixed to the base unit 20 also allows identification of the pill dispensing system 10 by a remote RFID tag reader being located at an external monitoring system of a pharmacy or a hospital. For the same purpose of identification by an external monitoring system, a serial number is provided to the base unit 20 during its manufacture.

Particularly, at the moment that the pill container 30 is mounted on the base unit 20, the RFID tag reader of the base unit 20 reads the RFID tag being affixed to the pill container 30 such that the base unit 20 identifies the pill container 30. The base unit 20 is adapted to communicate by means of the RF transceiver 25 with an outside server in order to receive from the outside server prescribed treatment information corresponding to the above mentioned pill container 30 being mounted on the base 20. Particularly, the prescribed treatment information comprises information regarding the time and date that each one of the pill compartments 12 should be accessed by the patient according to the prescribed treatment being proposed by a physician. The prescribed treatment information is stored into the memory 26 of the base unit 20. In an embodiment, the base unit 20 comprises a plurality of light emitting diodes (LEDs), each of them being disposed proximate to a respective one of the pill compartments 12 and being connected to the microprocessor 24 and to the memory 26 in order to illuminate the respective pill compartment 12 when it is time that the patient must receive the at least one pill contained therein according to the prescribed treatment information being provided by the outside server for the above mentioned pill container 30. In an example, the illumination may be performed by glittering light being emitted by the above mentioned LEDs.

In case that the patient has not accessed a respective one of the pill compartments 12 according to the above mentioned treatment information, the base unit 20 is adapted to transmit a first alarm signal by means of the RF transceiver 25 to the above mentioned outside server. Particularly, the base unit 20 transmits the above mentioned signal only in the case that a first pill compartment opening signal and/or second pill compartment opening signal has not been generated in the microprocessor 24 at the precise period (or precise time) and date as indicated in the prescribed treatment information. If for example the patient access a respective one of the pill compartments 12 of the pill container 30 being identified by the base unit 20 at a time or date later or earlier than that being indicated in the prescribed treatment information being received by the outside server, the base unit 20 will transmit a first alarm signal to the outside server. Afterwards, the outside server may transmit a second alarm signal to the patient indicating that the patient has not accessed the respective one of the pill compartments 12 according to the prescribed treatment information. In an example, the above mentioned second alarm signal is transmitted to a mobile phone of the patient by means of a short message service (SMS), vocal message or email. Similarly, the above mentioned alarm signal may be transmitted to a pharmacist or a physician or a third party concerned about the compliant receipt of pills by the patient.

In an embodiment, the outside server may transmit a warning signal to the patient indicating the patient must take some pills according to the prescribed treatment information. In an example, the warning signal is transmitted to a mobile phone of the patient by means of a short message service (SMS), vocal message or email. This warning signal is complementary to the lights warning or sound warning.

In an embodiment, the base unit 20 comprises a wireless communication module for the purpose of communicating wirelessly with the outside server. Particularly, the base unit 20 is adapted to receive a SIM card such that it can exchange information with the outside server by using the General Packet Radio Service (GPRS) technology.

In an embodiment, the pill dispensing system 10 comprises fastening means adapted to fasten the pill container 30 to the base unit 20. In an example, the base unit 20 is provided with a rotatable handle having a hook at the end thereof and with a hook receiving member being appropriately arranged to receive the hook of the rotatable handle in order to fixedly mount the pill container 30 onto the base unit 20. In another example, the base unit 20 is provided with a side magnetic flap.

In an embodiment, the base unit 20 comprises a signalling device being adapted to transmit an acoustic or optical signal when the pill container 30 is not properly fastened to the base unit 20.

FIGS. 4 to 8 illustrates an other embodiment of a pill dispensing system 100 for monitoring compliant receipt of pills by a patient. As previously, the pill dispensing system 100 includes a base unit 200 and a pill container 300 and has essentially the same operation.

Figure 4:
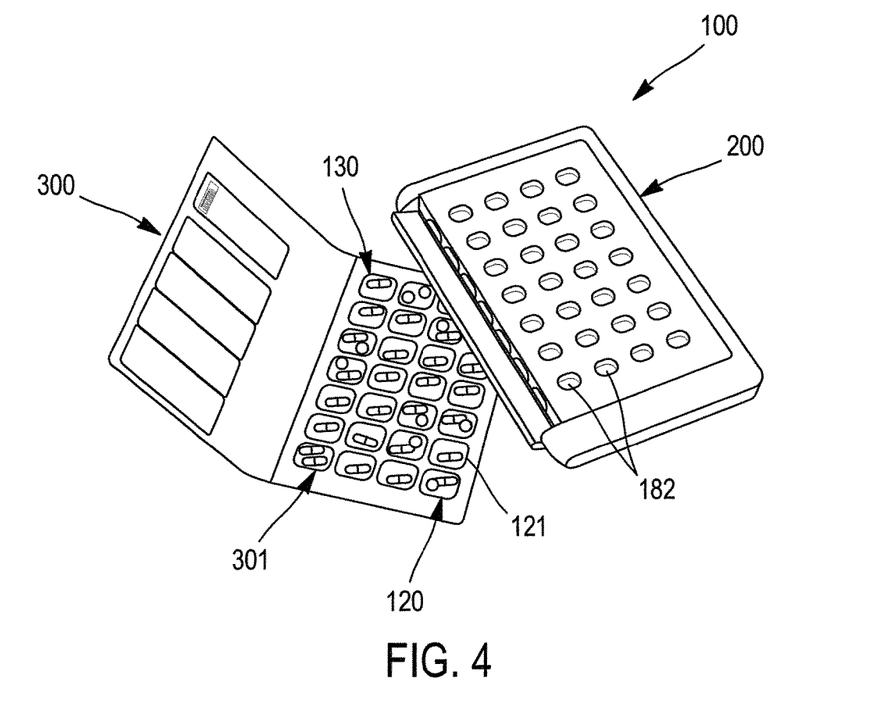
FIG. 4 illustrates a pill dispensing system according to an other embodiment of the invention showing the base unit and the pill container dissociated of the base unit.

The base unit 200 is in the form of a box substantially having a parallelepiped shape. The base unit 200 comprises an internal area 110 arranged to receive the pill container 300. As this will be understood later, the pill container 300 is inserted by sliding into the internal area 110 of the base unit 200. The base unit 200 further includes horizontal transverse partitions 181 (also named separation wall 181) dividing the area for receiving the pill container 300 in transverse compartments (180*a* to 180*f*). As this will be appreciated below, each transverse compartment (180*a* to 180*f*) is intended for receiving a row of compartments of the pill container 300. The horizontal partitions 181 extending from the top wall 201 of the base unit 200 to the vicinity of the bottom wall 202. To allow passage of the pill container 300, an appropriate distance, i.e. longer than or equal to the thickness of the flat support 301 of the pill container 300, that will be described later, is provided between the free end of the horizontal partitions 181 and the inner face of the bottom wall 202.

The upper wall 201 of the base unit 200 has a plurality of through holes 182 allowing to see the pills when the pill container 300 is received into the reception area 180 of the base unit 200. The through holes 182 which are aligned in a matrix form, respectively, are arranged to open in one of the compartments of the base unit 200, each horizontal row of holes being placed face to face a transverse compartment. As this will be understood, the through holes 182 are arranged to face the pill compartment of pill container 300.

The upper wall 201 and the horizontal transverse wall 181 form a motherboard of the unit base 200.

Figure 6:
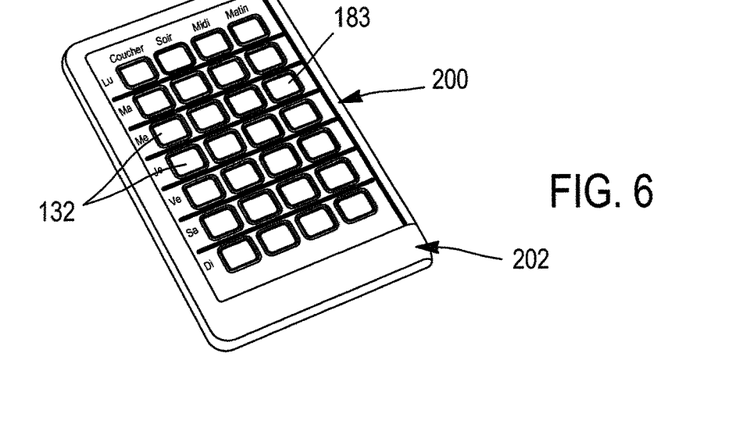
FIG. 6 illustrates a rear view of the base unit containing the pill container.
Figure 7:
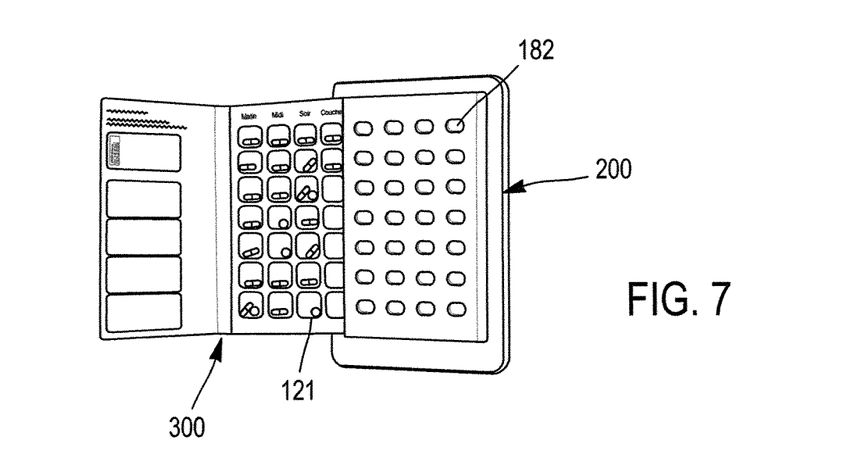
FIG. 7 illustrates a view of the pill container partially received in the base unit.
Figure 8:
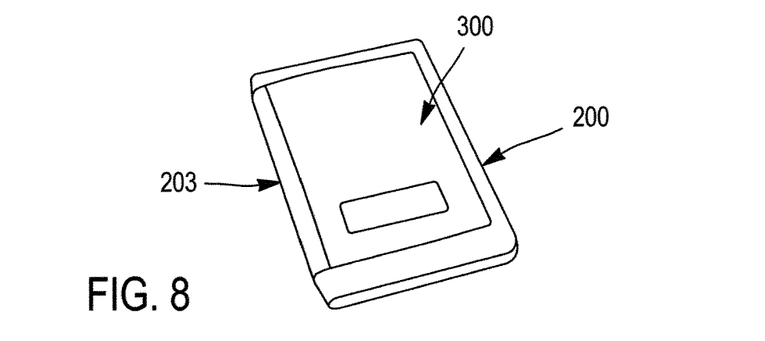
FIG. 8 illustrates a view of the pill dispensing system ready to be used, the pill container being entirely inserted into the base unit.

On the same manner, the bottom wall 202 of the base unit 200 has a plurality of through holes 183 allowing access to the pills when the pill container 300 is received into the reception area 180 of the base unit 200 (FIG. 6). More specifically, the through holes 183 are aligned in a matrix form so that to be face to face the through holes 183 of the upper wall 201 when the pill container 300 is not in position into the base unit 200. When the pill container is placed into the receiving area 110 as illustrated in FIG. 6, each through hole 183 is face to face to the area 132 of the pill compartment of the pill container intended to be opened to allow the access to the pills contained into the pill compartments. The through holes 183 have advantageously a diameter which correspond to a finger whereas the through holes 182 have a diameter smaller so that a finger (index finger, thumb, middle finger) could not be passed through them.

Figure 5:
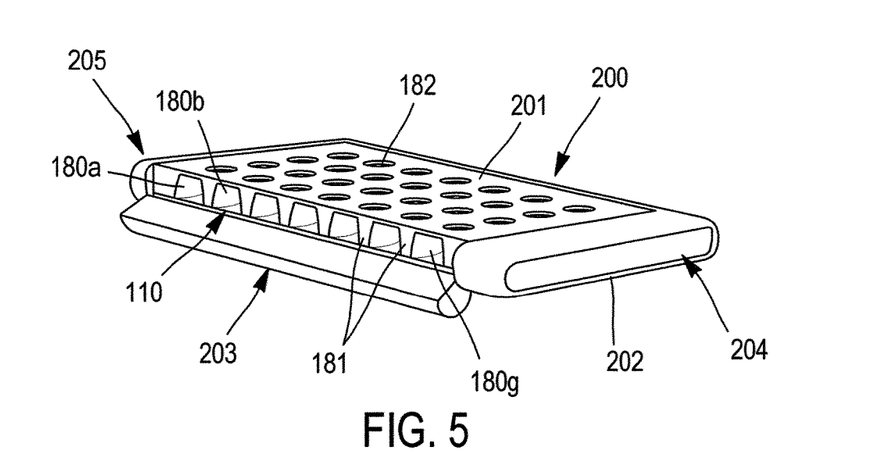
FIG. 5 illustrates a perspective lateral view of the base unit of the pill dispensing system of FIG. 4.

In the illustrated embodiment, the insertion of the pill container 300 is implemented by one of the side faces of the base unit 200. In the illustrated embodiment, the side wall 203 by which the pill container 300 is inserted, is a folding lateral wall 203. More particularly, the wall 203 is rotatable mounted between the two transverse walls 204, 205 of the base unit 200 about a longitudinal axis so as to pass from a closed position in which said folding wall is folded back against the top wall (FIG. 8) and a open position (FIGS. 4 and 5). According to another embodiment, the lateral wall 203 is removable. Of course it can be provided a base unit 200 having at least one open side face (i.e. a lateral face not closed). There may be also provided a base unit 200 having two side faces open, the pill container 300 being inserted indifferently by one or other of the faces. However the advantage of the presence of a removable or foldable wall allows to ensure insertion of the pill container 300 in the base unit 200 on the one hand and the retention of the pill container 300 into said base compartment on the other hand.

Also there may be provided a pill dispensing system allowing the insertion of pill container 300 by one of the transverse faces of the base unit 200 (insertion in a longitudinal direction to the base unit 200 and not by one of the side faces of the base unit 200 (insertion in a direction transverse to the base management unit).

In the described embodiment, the pill container 300 is in the form of a blister pack. More particularly, the pill container 300 comprises a flat support 301 carrying the pill compartments, said compartments being some recesses like for example shells 121 intended to receive pills. The face of the flat support 301 opposed to the face carrying the shells 121 is covered with a breakable closure film. The closure film is made of a paper material adapted to be pierced under the appropriate finger pressure. So, when an appropriate finger pressure is exerted to the film in the area covering the opening of the shells 121, the film can be pierced and thereby allow access to the pills contained in the shells 121. Advantageously, the shells 121 are made of transparent plastic. Of course this is one possible configuration of the pill container, and the embodiment in which the compartments are formed by recesses as in the example illustrated in FIGS. 1 to 3, can be used with a base unit 200 as described above. In this case the height of the horizontal partitions should be adapted to allow insertion of the pill container 300 in the base unit 200.

As above described, the pill container 300 comprises an array of twenty-eight pill compartments having four columns and seven rows. In that example each column may be labelled for a certain time period during the day (morning, midday, evening, bedtime) while each row may be labelled for a certain day of the week such that each pill compartment 12 corresponds to a certain day of the week and to a certain time period during the day. Each one of the pill compartments 12 may contain at least one pill being prescribed to the patient. Similarly, the base unit 200 has an upper wall having an arrangement of four columns and seven rows of through holes contents, each row of holes opening to one of said compartments.

As in the embodiment previously described, a RFID tag is affixed to the pill container 300 and an RFID tag reader is affixed to the base unit 200 for the purpose of identification of the pill container 300 by the base unit 200. Also, a RFID tag may be affixed to the base unit 200 for the purpose of identification of the base unit 200 by the RFID tag reader affixed to pill container 300 but also by a remote RFID tag reader being located at an external monitoring system. Data regarding the identity of the pharmacist who has delivered the pill dispensing system 100 to the patient and also regarding the identity of the patient who has received the pill dispensing system is encoded into the RFID tag being affixed to the base unit 200. The RFID tag affixed to the base unit 200 also allows identification of the pill dispensing system 100 by a remote RFID tag reader being located at an external monitoring system of a pharmacy, a hospital or in a remote information platform such as described later.

As in the embodiment previously described, the base unit 200 further comprises a plurality of optical detectors, comprising respectively an emitter 16 and a receiver 17. In the illustrated embodiment, the optical detectors are placed on the horizontal separation wall 181.

The base unit 200 further comprises an accelerometer connected to the microprocessor 24. The accelerometer is used to detect a change of state of the pill container 300. When it detects such a change of state, he generates some signals in relation with the change of state detected on the microprocessor 24. More particularly, when he detects an appropriate finger pressure to pierce a blister, the accelerometer identifies a change of state. The accelerometer generates a first signal on the microprocessor 24 which starts an algorithm process of detection of taking of pills. The algorithm process starts the optical detector 15 associated with the shell 121 of the pill container 300. As the embodiment previously described, the optical detector generates a pill compartment opening signal in response to the detection of the variation of the reflected light beam occurring after the removal of the at least one pill from the respective one of shells 121. The pill compartment opening signal is generated to the microprocessor 24. When the pill compartment is empty, there are not reflected signals any more. The microprocessor generates stopping the algorithm process. The accelerometer allows to detect piercing of the shell 121 containing the pills and in response to start the functioning of the optical detector via an algorithm process. The optical detector associated with algorithm process allows to identify that the patient has taken or not his treatment by some means that comprise a volume measurement. In the illustrated embodiment, the accelerometer replaces the breakable conductors 14 provided with the breakable closure 13. But the accelerometer may be also used in addition with the breakable conductors 14. The advantage of an accelerometer is that the level of breaking of shells 121 is accurate. Furthermore, the accelerometer allows to optimize consumption of the battery and the electronic components and to implement a panic mode without SOS button (panic mode activated by jerks). Moreover it allows to detect a fall and make up an alert to an information platform which will be described later.

The base unit 200 further comprises an altimeter connected to the microprocessor 24. The altimeter is used to take into account atmospheric pressure. The data from the altimeter are crossed with the data from the accelerometer.

Advantageously the base unit 200 comprises some means for enabling data transfer in Bluetooth/Wi-Fi/GPRS/Sigfox mode so that the data are transferred from the unit base to an external device or a system (such as an remote information platform dedicated to health data management as described below) equipped with Bluetooth/Wi-Fi/GPRS/Sigfox/Internet connection.

In addition, it may be provided that the base unit receive through a USB port or in Bluetooth/Wi-Fi/GPRS/Sigfox mode data coming from external device or from an information platform dedicated to health data management as described below.

Advantageously, the base unit 200 is provided with a USB port for enabling an user to connect it to any external device via a cable.

Figure 9:
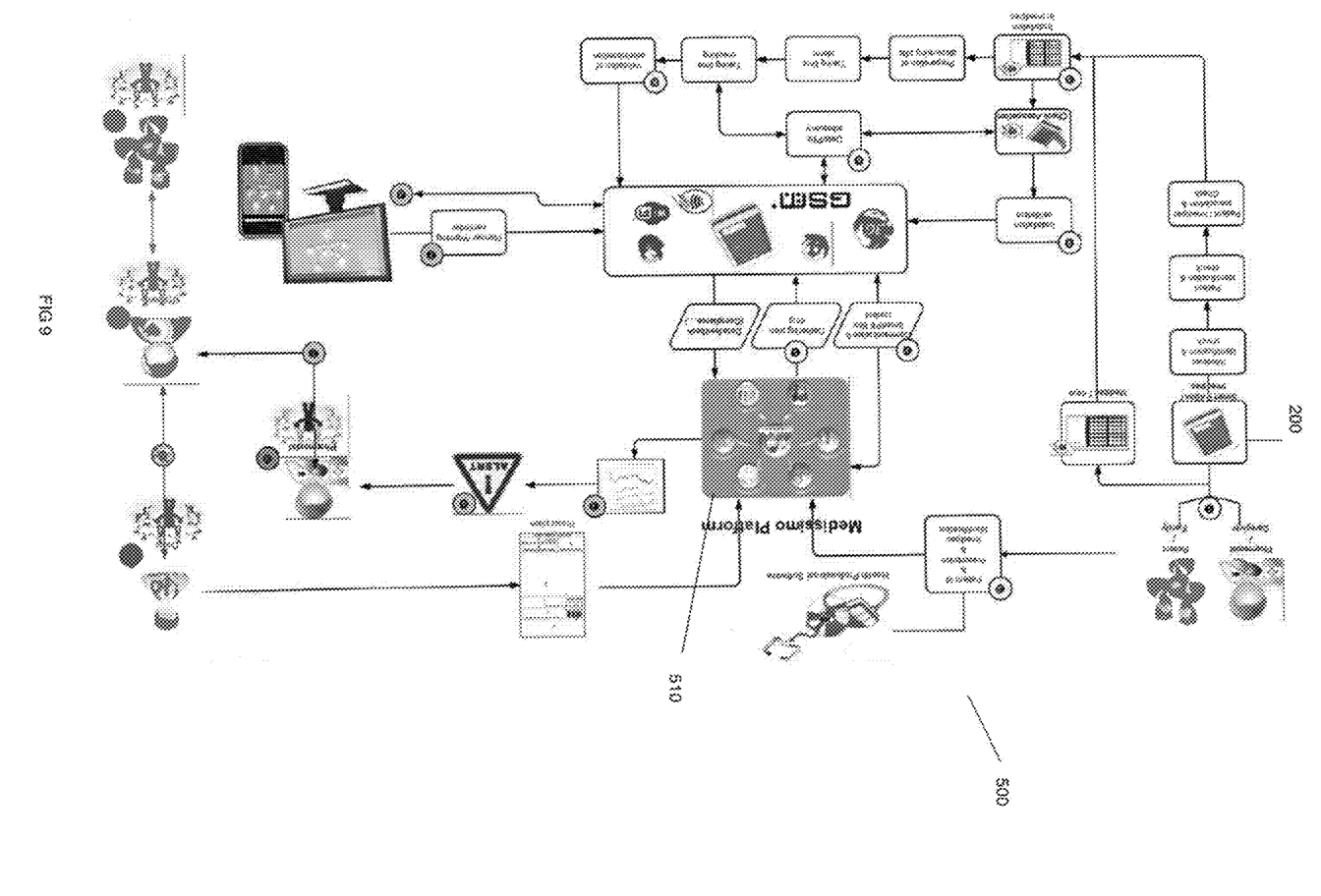
FIG. 9 illustrates en example of architecture of the information platform implemented with the pill dispensing system of FIGS. 1 to 8.

FIG. 9 illustrates an example of architecture of an information system 500 intended to be implemented with the pill dispensing system 100 and allowing the management, follow-up and so the traceability of the prescription and dispensing of pills to a patient.

The information system 500 comprises an information platform 510 grouping several databases such as base unit database, patient database, business rules, caregivers database, drug database, etc. As it will be understood later, the information platform 510 may receive data from the base unit 200 (data feedback such as taking or not, time of taking, etc), the pharmacist/caregiver/physician (data associated with the prescription and the patient). In addition, the information platform 510 may communicate some data to the base unit 200, pharmacist (especially some alerts). The information platform 510 further comprises a processing unit allowing to define the plan of taking from the content of the prescription (taking time, range to take the pills) and the plan of lighting to inform the patient that he must take the pills and to indicate the compartment 180*a* to 180*f* of the pill container concerned by the taking.

The management and the follow-up of the prescription and dispensing of pills to a patient are operated through the information system as following.

First of all the prescription may be traced at home, pharmacy or anywhere else by information system platform. To do this, the user (for example the pharmacist when the prescription is registered by the pharmacist) connects himself to the information platform 510 with his personal user name. Once identified, the user registers the identification of the pill container 300 and the content of the prescription in relation with the patient identification in the information platform. Once all information about the prescription filled in, the user fills the pill container according to the prescription, seals the compartments and delivers the pill container to the patient. The patient inserts the pill container 300 in the base unit 200. When the pill container 300 is inserted into the base unit 200, this latter identifies the pill container 300. From the identification of the pill container, the base unit 200 is going to query the information platform which, in response, is going to send to the unit base 200 the plan of taking of pills (downloading of cells, taking time).

The base unit 200 alerts patient of the taking time via some lights warning or ring or both. Each time patient burst blister for taking pills, the base unit 200 notifies information platform about the taking time. If patient miss taking time, warning is provided to the information platform, and sent to identify addresses (information platform is able to raise alerts to pharmacist in case of takes default). Advantageously, the recorded observance data are available to patient, pharmacy and, with the patient's agreement, to physician or caregivers or relatives.

In the foregoing, the prescription is recorded by the pharmacist in the information platform. The advantage of this process is that the prescription, like for example the take quantity, the take timing, can be modify directly in the information platform. According to an alternative embodiment, the content of the prescription can be recorded directly into the RFID chip of the base unit 200. In this case, the RFID chip is a reading and writing chip.

Figure 2:
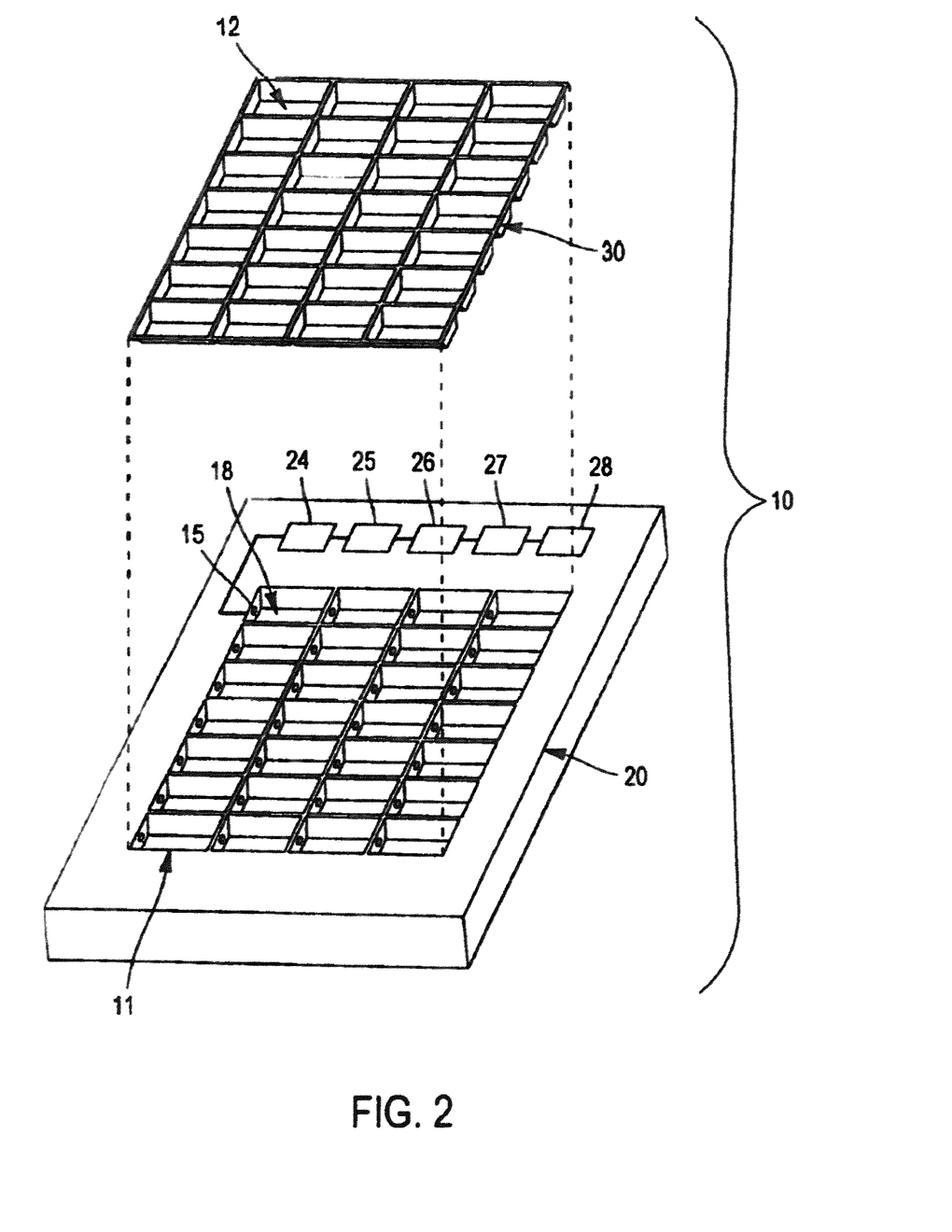
FIG. 2 illustrates an exploded view of the pill dispensing system of the embodiment of FIG. 1 showing the base unit and the pill container of the pill dispensing system.

In the foregoing, the pill dispensing system is implemented with a configuration wherein the pill container 300 is inserted into the base unit 200. Of course the pill dispensing system can be implemented with other configurations of the pill container 300 and base unit 200. In particular, the pill dispensing system can be implemented with a pill container 300 be able to plug into a base unit 200 as shown in FIGS. 1 to 3.

Moreover it should be noted that the pill container 300 can be also used without the base unit if necessary.

The invention claimed is:

1. A pill dispensing system for monitoring compliant receipt of pills by a patient, comprising
   a base unit having an area adapted to receive a pill container,
   a pill container comprising an array of a plurality of pill compartments, at least one pill compartment containing at least one pill and said area comprising an array of a plurality of compartments adapted to receive at least one of said pill compartments, said base unit comprising a microprocessor and a power supply, said pill container comprising at least one breakable closure sealing at least one of said pill compartments,
   means for detecting breaking of the breakable closure of a respective one of the pill compartments and for generating a first pill compartment opening signal on the microprocessor upon breaking of the breakable closure of a respective one of the pill compartments,
   each compartment being associated with a respective means for detecting the removal of the at least one pill from said pill compartments upon breaking of the breakable closure of said pill compartments and for generating a second pill compartment opening signal on the microprocessor upon the removal of the at least one pill from said pill compartments.

2. The pill dispensing system according to claim 1, wherein said means for detecting the removal of the at least one pill from one of the pill compartments upon breaking of the breakable closure of the respective one of the pill compartments and for generating a second pill compartment opening signal on the microprocessor comprise a plurality of optical detectors, each optical detector being associated with a respective one of the pill compartments of the pill container when the pill container is received by said base unit.

3. The pill dispensing system according to claim 1, wherein an optical detector comprises an emitter and a corresponding receiver being proximately disposed on a lateral side of a respective one of the pill compartments when the pill compartments are fixed to said base unit, said emitter emitting a light beam being reflected at a surface of the at least one pill when the associated pill compartment comprises at least one pill and being received by a receiver, said optical detector being adapted to generate the second pill compartment opening signal in response to the detection of a variation of the reflected light beam occurring after the removal of the at least one pill from the respective one of the pill compartments upon breaking of the breakable closure of the respective one of the pill compartments.

4. The pill dispensing system according to claim 1, wherein said means for detecting the breaking of the breakable closure of a respective one of the pill compartments and to generating a first pill compartment opening signal on the microprocessor comprise at least one breakable conductor, each breakable conductor being provided with the at least one breakable closure sealing at least one of said pill compartments and arranged to be associated with a respective one of the pill compartments of the pill container.

5. The pill dispensing system according to claim 1, wherein said means for detecting the breaking of the breakable closure of a respective one of the pill compartments and to generating a first pill compartment opening signal on the microprocessor comprise an accelerometer.

6. The pill dispensing system according to claim 1, wherein the compartments of said area are arranged to form an array of a plurality of recesses equivalent to the array of the plurality of pill compartments of the pill container.

7. The pill dispensing system according to claim 2, wherein the base unit comprises a RF transceiver being adapted to communicate at least one of the first pill compartment opening signal and the second pill compartment opening signal to an outside server.

8. The pill dispensing system according to claim 2, wherein the base unit comprises a memory and a clock, the memory being adapted to store information relating to the time of breaking of the breakable closure of a respective one of the pill compartments.

9. The pill dispensing system according to claim 1, wherein the base unit comprises a wireless communication module arranged to allow wireless communication with an outside server.

10. The pill dispensing system according to claim 1, wherein a RFID tag is affixed to the pill container and an RFID tag reader is affixed to the base unit for the purpose of identification of the pill container by the base unit.

11. The pill dispensing system according to claim 1, wherein a RFID tag is affixed to the base unit for the purpose of identification of the base unit by a RFID tag reader.

12. The pill dispensing system according to claim 2, comprising a plurality of light emitting diodes, each light emitting diode being disposed proximate to a respective one of the pill compartments for illuminating the respective one of the pill compartments at a predetermined time of scheduled receipt of the pills contained in the respective one of the pill compartments.

13. The pill dispensing system according to claim 1, comprising fastening means adapted to fixedly mount the pill container onto the base unit.

14. The pill dispensing system according to claim 1, wherein the breakable closures are made of a conductive material.

15. The pill dispensing system according to claim 2, wherein the breakable closures are made of a nonconductive material.

16. The pill dispensing system according to claim 2, wherein the pill container is a single-use container.

\* \* \* \* \*